United States Patent [19]
Preissman et al.

[11] Patent Number: 6,019,776
[45] Date of Patent: Feb. 1, 2000

[54] PRECISION DEPTH GUIDED INSTRUMENTS FOR USE IN VERTEBROPLASTY

[75] Inventors: Howard Preissman, San Jose, Calif.; Mary E. Jensen, Croget; Jacques E. Dion, Charlottsville, both of Va.

[73] Assignee: Parallax Medical, Inc., San Jose, Calif.

[21] Appl. No.: 08/950,382

[22] Filed: Oct. 14, 1997

[51] Int. Cl.$^7$ ..................................................... A61B 17/34
[52] U.S. Cl. ........................... 606/185; 600/567; 604/165
[58] Field of Search ..................................... 600/562, 564, 600/565, 566, 567; 604/164, 165, 170; 606/170, 171, 184, 185, 61, 73; 623/16, 17

[56] References Cited

U.S. PATENT DOCUMENTS

| | | | |
|---|---|---|---|
| 4,469,109 | 9/1984 | Mehl . | |
| 4,670,008 | 6/1987 | Von Albertini | 604/165 |
| 4,793,363 | 12/1988 | Ausherman et al. . | |
| 4,838,282 | 6/1989 | Strasser et al. . | |
| 5,014,717 | 5/1991 | Lohrmann . | |
| 5,195,526 | 3/1993 | Michelson . | |
| 5,341,816 | 8/1994 | Allen | 600/567 |
| 5,372,583 | 12/1994 | Roberts et al. | 604/51 |
| 5,456,267 | 10/1995 | Stark | 128/898 |
| 5,660,186 | 8/1997 | Bachir . | |

FOREIGN PATENT DOCUMENTS 42 19 563 A1  12/1993  Germany .

OTHER PUBLICATIONS

Cotten et al., "Preoperative percutaneous injection of methyl methacrylate and N–butyl cyanoacrylate in vertebral hemangiomas" *Am J Neuroradiol* (1996) 17:137–142.

Cybulski, "Methods of surgical stabilization for metastatic disease of the spine" *Neurosurgery* (1989) 25:240–252.

Deramond et al., "Percutaneous vertebroplasty with methyl–methacrylate: technique, method, results" *Radiology* (1990) 117(supp.):352.

Galibert et al., "Note préliminaire sur le traitement des angiomes vertébraux par vertébroplastie acrylique percutanée" *Neurochirurgie* (1987) 33:166–168. (Partial summary translation included).

Harrington, "Anterior decompression and stabilization of the spine as a treatment for vertebral collapse and spinal cord compression from metastatic malignancy" *Clnical Orthodpaedics and Related Research* (1988) 233:177–197.

Kaemmerlen et al., "Vertébroplastie percutanée dans le traitement des métastases" *J. Radiol.* (1989) 70(10):557–562. (Partial summary translation included).

(List continued on next page.)

*Primary Examiner*—Michael Buiz
*Assistant Examiner*—David O. Reip
*Attorney, Agent, or Firm*—Morrison & Foerster

[57] ABSTRACT

Precision depth guided instruments are provided for use in performing percutaneous implantation of hard tissue implant materials. A depth guided stylet include a point adapted for piercing hard tissue, self-tapping threads for self-tapping into hard tissue, and, optionally, a second set of threads for meshing with threads within a overfitting cannula. The stylet may include an elongated rod having a first section having a first diameter, and a second section having a second diameter larger than the first diameter. A cannula for use with a depth guided stylet includes an elongated tube having first and second open ends adapted for a depth guided stylet to pass therethrough. The cannula may include threads along at least a portion of an interior circumference of the elongated tube, which are adapted to mate with threads on an exterior circumference of the depth guided stylet. Alternatively, a set of intersecting grooves may be included in the handle of the cannula to mate with a protrusion on the handle of the stylet. A method of using the instruments is also disclosed, as is a kit which includes the instruments and which is used to open a pathway into hard tissue.

16 Claims, 14 Drawing Sheets

OTHER PUBLICATIONS

Nicola et al., "Vertebral hemangioma: Retrograde embolization—Stabilization with methyl methacrylate" *Surg Neurol* (1987) 27:481–486.

O'Donnell et al., "Recurrence of giant–cell tumors of the long bones after curettage and packing with cement" *J. of Bone and Joint Surg* (1994) 76–A(12):1827–1833.

Persson et al., "Favourable results of acrylic cementation for giant cell tumors" *Acta Orthop Scand* (1984) 55:209–214.

Shapiro, "Cranioplasty, vertebral body replacement, and spinal fusion with tobramycin–impregnated methyl-methacrylate" *Neurosurgery* (1991) 28(6):789–791.

Stringham et al., "Percutaneous transpedicular biopsy of the spine" *Spine* (1994) 19(17):1985–1991.

Sundaresan et al., "Treatment of neoplastic epidural cord compression by vertebral body resection and stabilization" *J. Neurosurg* (1985) 63:676–684.

Wang et al., "Safety of anterior cement fixation in the cervical spine: In vivo study of dog spine" *So. Medical J.* (1984) 77(2):178–179.

Weill et al., "Spinal metastases: Indications for and results of percutaneous injection of acrylic surgical cement" *Radiology* (1996) 199(1):241–247.

PRECISION DEPTH GUIDED INSTRUMENTS FOR USE IN VERTEBROPLASTY

CROSS-REFERENCE TO RELATED APPLICATIONS

The present application is related to application, filed concurrently herewith, application Ser. No. 08/949,839.

TECHNICAL FIELD

The present invention relates to instruments for more accurately controlling the placement thereof, during surgical procedures for the repair of hard tissue by injection of hard tissue implant materials. Procedures for such repair include hip augmentation, mandible augmentation, and particularly vertebroplasty, among others.

BACKGROUND ART

Polymethylmethacrylate (PMMA) has been used in anterior and posterior stabilization of the spine for metastatic disease, as described by Sundaresan et al., "Treatment of neoplastic epidural cord compression by vertebral body resection and stabilization." *J Neurosurg* 1985;63:676–684; Harrington, "Anterior decompression and stabilization of the spine as a treatment for vertebral collapse and spinal cord compression from metastatic malignancy." *Clinical Orthodpaedics and Related Research* 1988;233:177–197; and Cybulski, "Methods of surgical stabilization for metastatic disease of the spine." *Neurosurgery* 1989;25:240–252.

Deramond et al., "Percutaneous vertebroplasty with methyl-methacrylate: technique, method, results [abstract]." *Radiology* 1990;117 (suppl):352; among others, have described the percutaneous injection of PMMA into vertebral compression fractures by the transpedicular or paravertebral approach under CT and/or fluoroscopic guidance. Percutaneous vertebroplasty is desirable from the standpoint that it is minimally invasive, compared to the alternative of surgically exposing the hard tissue site to be supplemented with PMMA or other filler.

The general procedure for performing percutaneous vertebroplasty involves the use of a standard 11 gauge Jamshidi needle. The needle includes an 11 gauge cannula with an internal stylet. The cannula and stylet are used in conjunction to pierce the cutaneous layers of a patient above the hard tissue to be supplemented, then to penetrate the hard cortical bone of the vertebra, and finally to traverse into the softer cancellous bone underlying the cortical bone.

A large force must be applied by the user, axially through the Jamshidi needle to drive the stylet through the cortical bone. Once penetration of the cortical bone is achieved, additional downward axial force, but at a reduced magnitude compared to that required to penetrate the cortical bone, is required to position the stylet/ tip of the cannula into the required position within the cancellous bone. If the force magnitude is not reduced appropriately, or if very soft bone is encountered, as is often the case with osteoporitic patients, the stylet and cannula can be accidentally and suddenly driven through the cortical bone on the opposite side of the vertebra. This is a very dangerous and potentially lethal situation in the case of vertebroplasty, since the aorta is located in close proximity to the anterior surface of at least the thoracic and lumbar vertebrae, and could easily be punctured by such an occurrence. Additionally, with regard to all vertebrae, the spinal cord is located medially of the pedicle, and could also be damaged by a piercing stylet.

Accordingly, there exists a need for a more controlled approach to the interior of a vertebral body for the performance of vertebroplasty and particularly, percutaneous vertebroplasty.

DISCLOSURE OF THE INVENTION

Disclosed are instruments for percutaneously accessing hard tissue to deliver a hard tissue implant material thereby. A depth guided stylet includes an elongated rod having first and second ends and a longitudinal axis. The first end terminates in a point adapted for piercing hard tissue. A handle is provided on the second end of the elongated rod for providing a mechanical advantage to a user in rotating the elongated rod about the rod's longitudinal axis.

Self-tapping threads extend from the point along the elongated rod for a predetermined distance. The self-tapping threads are adapted to self-tap into hard tissue. A second set of threads may be provided on the elongated rod in a location between the self-tapping threads and the handle. The second set of threads are adapted to mate with a set of threads within a cannula that fits over the elongated rod.

Alternatively, the elongated rod may have a first section having a first diameter, and a second section having a second diameter larger than the first diameter. In this alternative arrangement, the self-tapping threads are provided on the first section, and the second set of threads, if present, are provided on the second section.

A cannula for use with a depth guided stylet is also disclosed. The cannula includes an elongated tube having first and second ends. The first and second ends are open and adapted for a depth guided stylet to pass therethrough. The cannula further includes a handle attached to the second end of the elongated tube, which is used for torquing and or pushing the cannula.

Means for positioning the elongated tube of the cannula with respect to the depth guided stylet are provided to include, in one embodiment, threads along at least a portion of an interior circumference of the elongated tube. The threads on the elongated tube of the cannula are adapted to mate with threads on an exterior circumference of the depth guided stylet.

Alternatively, the means for positioning the elongated tube of the cannula may include a set of intersecting grooves in the handle of the cannula. The set of intersecting grooves including at least a pair of intersecting grooves having different depths. The grooves are adapted to fit over a protrusion on a handle of the depth guided instrument to set the position of the cannula at a predetermined location along the depth guided stylet.

A kit which is adapted to open a pathway into hard tissue is disclosed to includea depth guided stylet and a cannula. The depth guided stylet includes an elongated rod having first and second ends and a longitudinal axis. The first end of the elongated rod of the stylet terminates in a point adapted for piercing hard tissue. A first positioning element is included on a predetermined location of the stylet. Self-tapping threads, adapted to self-tap into hard tissue, extend from the stylet point along the elongated rod for a predetermined distance.

The cannula of the kit includes an elongated tube having first and second ends which are open and adapted for the depth guided stylet to pass therethrough. A second positioning element is on a predetermined location of the cannula. The second positioning element is adapted to interact with the first positioning element to define a position of the cannula with respect to the stylet.

Preferably, the first positioning element includes a second set of threads on the elongated rod of the stylet in a location between the self-tapping threads and the second end of the elongated rod. Preferably, the second positioning element includes cannula threads along at least a portion of an interior circumference of the elongated tube of the cannula. The cannula threads are adapted to mate with the second set of threads on the stylet.

The depth guided stylet further comprises a handle provided on the second end for providing a mechanical advantage to a user in rotating the elongated rod about its longitudinal axis. The cannula further includes a handle provided on the second end of the elongated tube.

Alternatively, the first positioning element may include a protrusion on the handle of the stylet, and the second positioning element may include a set of intersecting grooves in the handle of the cannula. The set of intersecting grooves includes at least a pair of intersecting grooves having different depths. The grooves are adapted to fit over the protrusion of the handle to set the position of the cannula at a predetermined location along the depth guided stylet.

A connector is provided on the handle of the cannula for connecting the cannula to tubing following removal of the stylet from within the cannula Preferably, the connector includes a Luer lock type fitting, although alternative types of connectors may be used.

Optionally, the elongated tube of the cannula may have a first section having a first diameter, and a second section having a second diameter larger than the first diameter, with the first section being closer to the first end of the elongated tube than the second section. Additionally, the elongated rod may optionally include a first rod section having a first rod diameter, and a second rod section having a second rod diameter larger than the first rod diameter, with the self-tapping threads being provided on the first rod section, and the second set of threads being provided on the second rod section. The cannula threads are provided on the second tube section under this option.

Also disclosed is a method of percutaneously implanting a hard tissue implant material, which includes inserting a stylet having self-tapping threads, and a cannula, percutaneously and through the soft tissues of an organism until abutting hard tissue. The stylet is next torqued to engage the self-tapping threads in the hard tissue to draw the stylet through the hard tissue and into a predetermined location within the hard tissue. Next, the cannula is advanced along the stylet to the predetermined position. Once the cannula has been placed in the predetermined position, the stylet is withdrawn from within the cannula while maintaining the cannula in the predetermined position.

Preferably the cannula has threads along at least a portion thereof and the stylet has a second set of threads that mesh with the threads of the cannula, and the advancement of the cannula is accomplished by torquing the cannula with respect to the stylet to engage the cannula threads with the second set of threads of the stylet, thereby driving the cannula to the predetermined position.

BEST MODE FOR CARRYING OUT THE INVENTION

Figure 1:
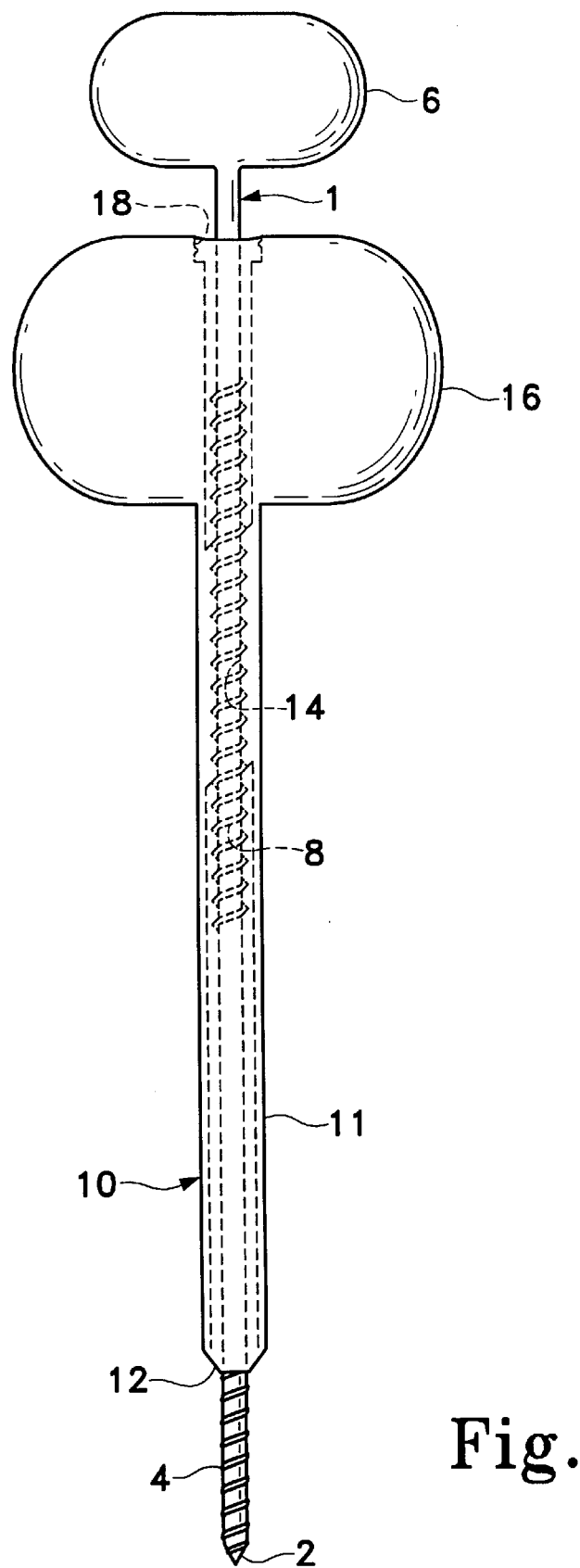
FIG. 1 is a plan view of a preferred embodiment of the depth guided stylet and cannula according to the present invention.

The present invention substantially reduces several of the risk factors associated with the performance of percutaneous vertebroplasty. Additionally, the present invention enables a reduction in amount of pressure which must necessarily be applied to both the stylet and cannula, as well as the "filler" to be implanted via the cannula.

As noted above, the general procedure for performing percutaneous vertebroplasty involves the use of a standard 11 gauge Jamshidi needle, illustrated as reference numeral 100 in the prior art illustration of FIGS. 8–11. The needle 100 includes an 11 gauge cannula 101 with an internal stylet 102. The cannula 101 and stylet 102 are used in conjunction to pierce the cutaneous layers of a patient above the hard tissue to be supplemented, then to penetrate the hard cortical bone 103 of the vertebra, and finally to traverse into the softer cancellous bone 104 underlying the cortical bone.

A large force F must be applied by the user, axially through the Jamshidi needle to drive the stylet 102 through the cortical bone 103. Once penetration of the cortical bone 103 (through the pedicle of the vertebra in this example) is achieved, additional downward axial force, but at a reduced magnitude compared to that required to penetrate the cortical bone, is required to position the stylet/tip of the cannula into the required position within the cancellous bone, as shown in a progression from FIG. 9 to FIG. 10. If the force magnitude is not reduced appropriately, or if very soft bone is encountered, as is often the case with osteoporitic patients, the stylet and cannula can be accidentally and suddenly driven through the cortical bone 103 on the opposite side of the vertebra. In one of the worse case scenarios, the stylet may continue traveling beyond the cortical bone and into the aorta 105, which is a potentially lethal situation. Another potential risk, due to the large driving forces required, is that the stylet 102 could be driven askew and into the spinal cord 106 with the potential to cause permanent paralysis.

Because of the large forces required, it is not uncommon for the stylet to suddenly "break through" and make its pass through the cortical bone both very rapidly and very uncontrollably. Because of the speed with which such a break through can occur, it may be difficult if not impossible for the stylet operator to react in time to reduce the driving force. Consequently, the stylet may be driven through the opposite cortical bone layer almost simultaneously.

The present invention overcomes these inherent risks by providing instruments which can be driven through the cortical bone much more controllably and reliably. Less force is required to accomplish the placement of the instruments and, at the same time, the advancement of the instruments can be accomplished at a much slower and more controllable, consistent rate.

Turning to FIG. 1, a preferred example of depth guided instruments will now be described. A stylet 1 is provided which has a length that is more than sufficient to span the distance from the epidermis of a patient to the cancellous bone tissue in the vertebra, in the preferred configuration. Typically the length of the stylet would be about three inches or greater, but lesser lengths may also be employed as well, depending on the size of the patient. Of course, if other hard tissues are to be accessed, the length of the stylet can be readily modified without departing from the inventive features of the present invention.

The stylet 1 is preferably made of a surgical grade stainless steel, but other known equivalent biocompatible metals and materials may be used for the same purpose. Ideally, the stylet, or at least a distal end thereof, will be radiopaque so that it can be monitored using fluoroscopy, CT or other imaging techniques during the procedure to help determine the depth and location of the penetration.

Figure 12:
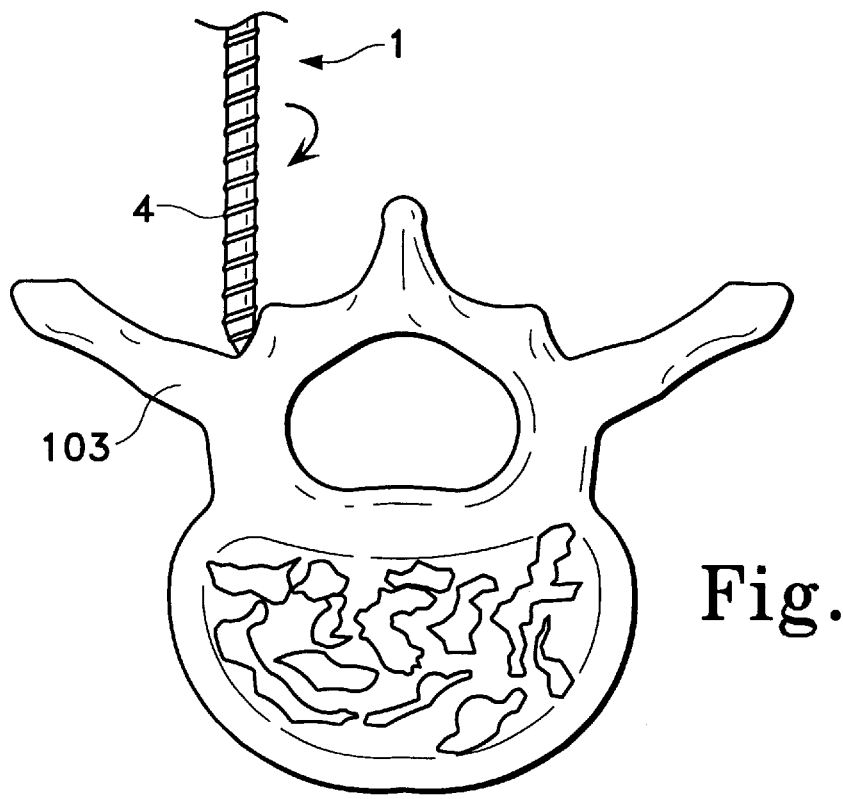
FIGS. 12, 13, 14, 15, 16 and 17 illustrate some of the advantages and risk reduction that are inherent in using the present invention.
Figure 13:
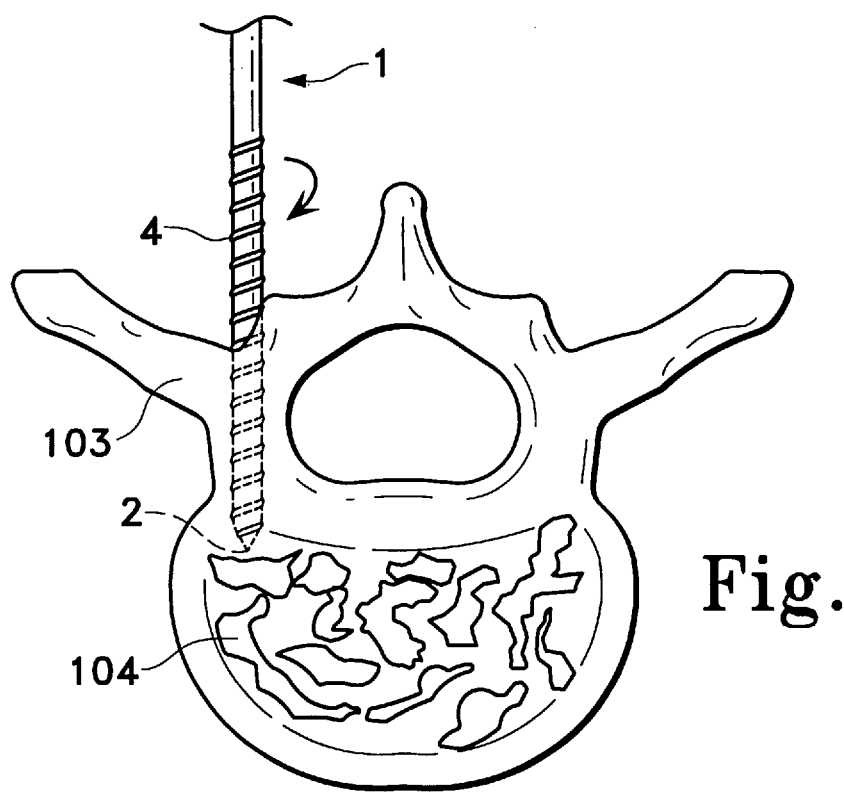

A first or distal end of the stylet 1 ends in a point 2 which is sharp and adapted to penetrate hard tissue when axially loaded. Extending from the tip 2 are self-tapping threads 4. The self-tapping threads 4 provide an advantage in that once the tip 2 has penetrated the cortical bone (e.g., see FIG. 12), the operator of the stylet can than proceed to advance the stylet by torquing the stylet, which engages the self-tapping threads 4 in the cortical bone 103 and begins to screw the stylet 1 into the cortical bone 103, as illustrated in FIG. 13.

The second or proximal end of the stylet preferably has a handle 6 molded or otherwise fixed thereto, to enable the operator to rotate or torque the stylet 1 about its longitudinal axis with a mechanical advantage. The handle 6 is preferably molded of polycarbonate. However, any other materials which are durable, sterilizable and biofriendly, could be readily substituted. For example, the handle could be made from nylon or a host of other well-known plastics suitable for this purpose, or stainless steel, titanium, other biocompatible metals and ceramics.

A cannula 10 is provided which includes an elongated tubular structure 11 to be positioned in the cancellous bone for delivery of PMMA or other bone implant material therein. The tubular structure 11 of the cannula 10 is preferably made of a surgical grade of stainless steel, but may be made of known equivalent materials, similarly to the stylet 1 discussed above. Preferably, at least a distal end of the tubular structure is radiopaque. The tubular structure 11 has an inside diameter which is only slightly larger than the outside diameter of the stylet 1, so that the cannula may effortlessly pass axially over the stylet, while at the same time being supported and guided by the stylet. A first or distal end 12 of the cannula is preferably (but not necessarily) beveled to ease the penetration of the cannula through the cutaneous and soft tissues, and especially through the hard tissues.

A second or proximal end of the cannula preferably has a handle 16 molded or otherwise fixed thereto, to enable the operator to rotate, torque or push the cannula 10. The handle 16 is preferably molded of polycarbonate. However, any other materials which are durable, sterilizable and biofriendly, as discussed above with regard to handle 6, could be readily substituted.

Figure 14:
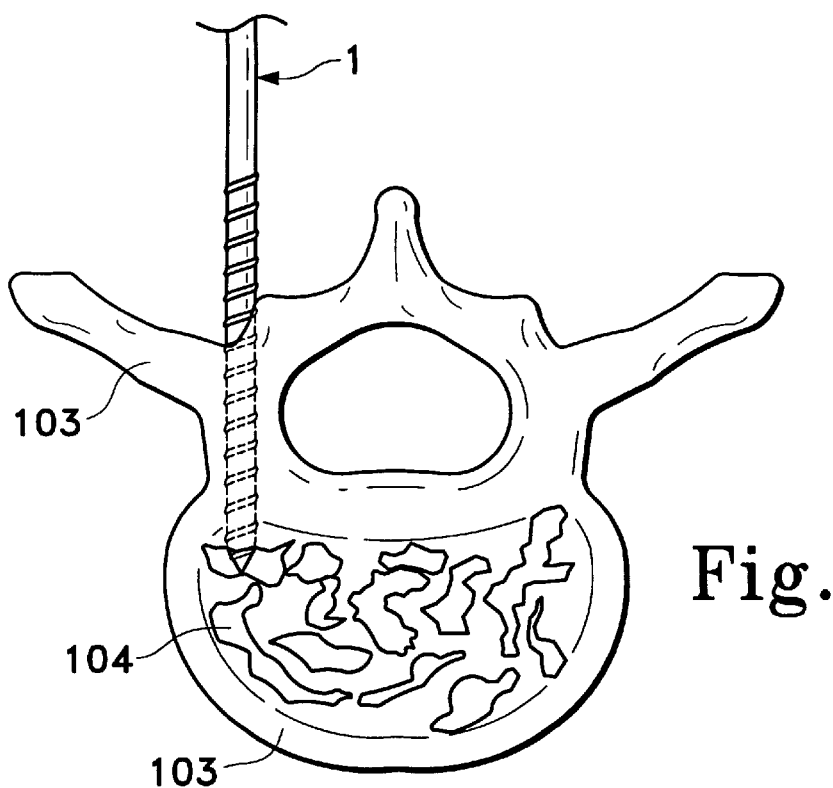

At least a portion of the inner circumference of the tubular structure of cannula 10 is provided with threads 14 which mate with a second set of threads 8 which are provided on the external circumference of stylet 1 distally of threads 4. The intermeshing of threads 8 and 14 provides a driving and control mechanism for the positioning, advancement and control of the cannula 10 with respect to the stylet 1 and vice versa. Thus, after screwing the stylet 1 into the desired position (e.g., the cancellous tissue of the vertebra as shown in FIG. 14) in the hard tissue, as confirmed by viewing the position using an imaging technique referred to above, the operator proceeds to grasp the handle 6 so as to prevent the stylet from rotating further.

Figure 15:
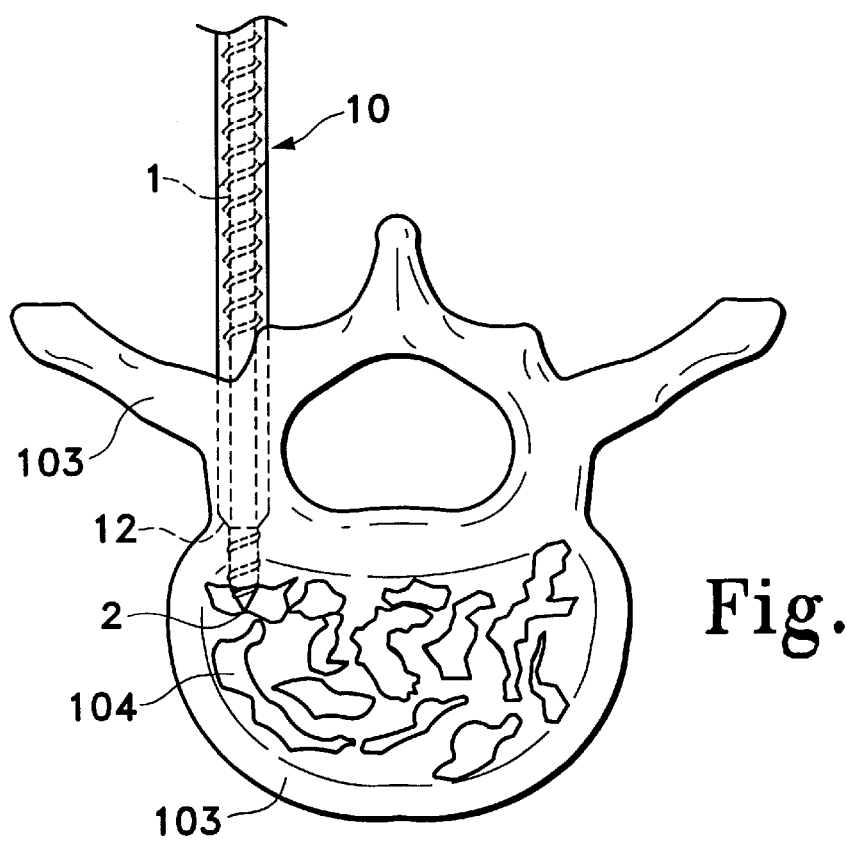
Figure 16:
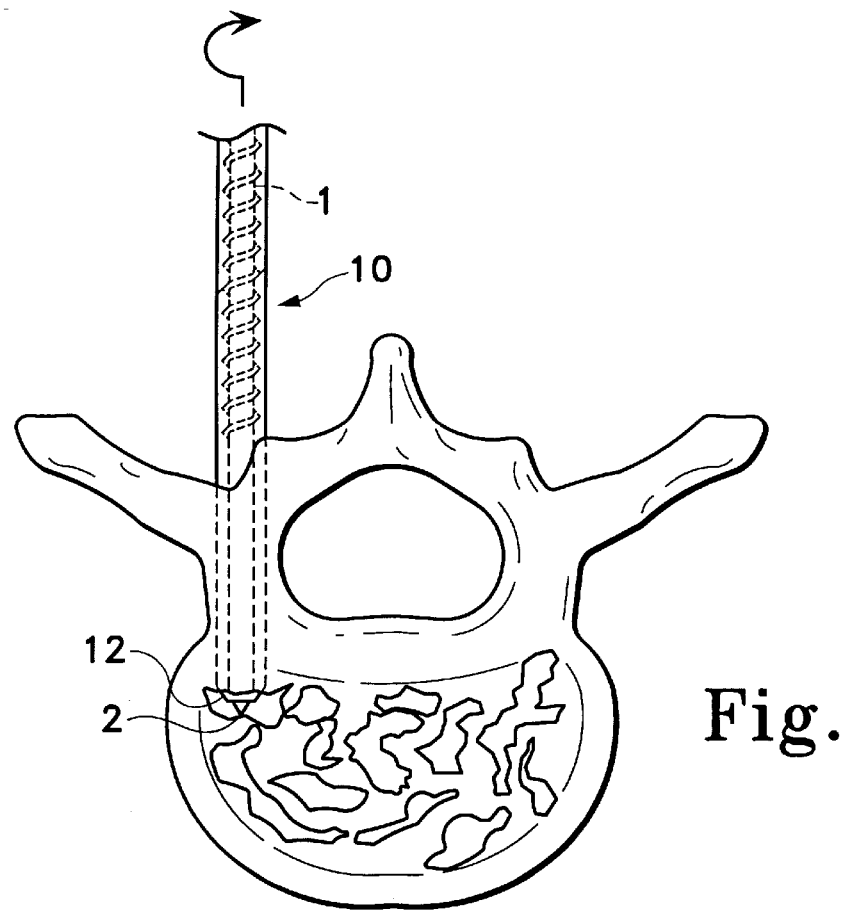

At the same time, the operator would rotate handle 16 in a clockwise rotation (or counterclockwise direction depending upon the handedness of the intermeshing threads 8 and 14, as would be readily apparent to one of ordinary skill in the art) to advance the beveled end 12 of the cannula in a direction toward the point of the stylet 2. This advancement is progressively shown in the partial views of FIGS. 14 and 15. The advancement of the cannula 10, and particularly the beveled end 12 are monitored using an imaging technique to ensure the proper placement of the cannula for injection of the PMMA or other hard tissue implant material. When the beveled end 12 is advanced to a position that is substantially flush with point 2, as shown in FIG. 16, the operator will cease the advancement of the cannula 10, since it will have reached its optimal position.

Figure 17:
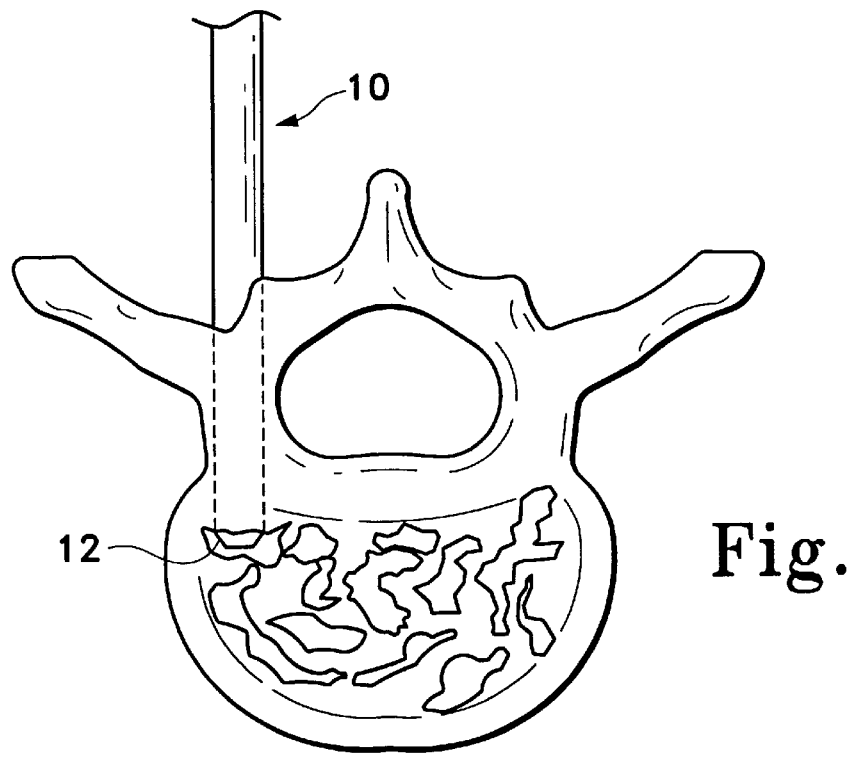

The operator next holds the handle 16 in a fixed, non-rotary position, while rotating the handle 6 in a rotation which is reverse of the direction that the handle 16 had been previously rotated in, so as to retract the stylet 1 from the site, while maintaining the cannula 10 in its position. The operator continues this process until the stylet 1 has been completely removed from within the cannula 10, as shown in FIG. 17.

An alternative method of inserting the cannula 10 would be to incrementally insert the stylet 1 and the cannula 10. More specifically, the operator could thread the stylet 1 only partially into the cortical bone 103 of the pedicle, and then advance the cannula 10 so as to be substantially flush or close to the tip 2 as described above. Then the operator would again advance the stylet for a small distance through the cortical bone, stop the advancement and follow with advancement of the cannula 10 by the same increment. This type of incremental advancement could be continued until the tip 2 and the beveled end reach the same desired location as described above and shown in FIG. 16. Incremental advancement may still further reduce the force that is necessary to be applied to advance the cannula 10 through the cortical bone 103. However, the incremental approach is more time consuming, which is a factor that must be considered in deciding whether or not to use the incremental approach.

Surrounding the second end of the tubular structure 11 is a connector 18 for linking the cannula 10 with a syringe or other tubular supply, for supplying the PMMA or other implantable material that is to be injected via tubular structure 11. Preferably, connector 18 is a Luer-lock type of connector, but other known connecting mechanisms may be successfully interchanged, e.g., a conventional threaded hole, a threads and locking nut arrangement, etc.

Figure 2:
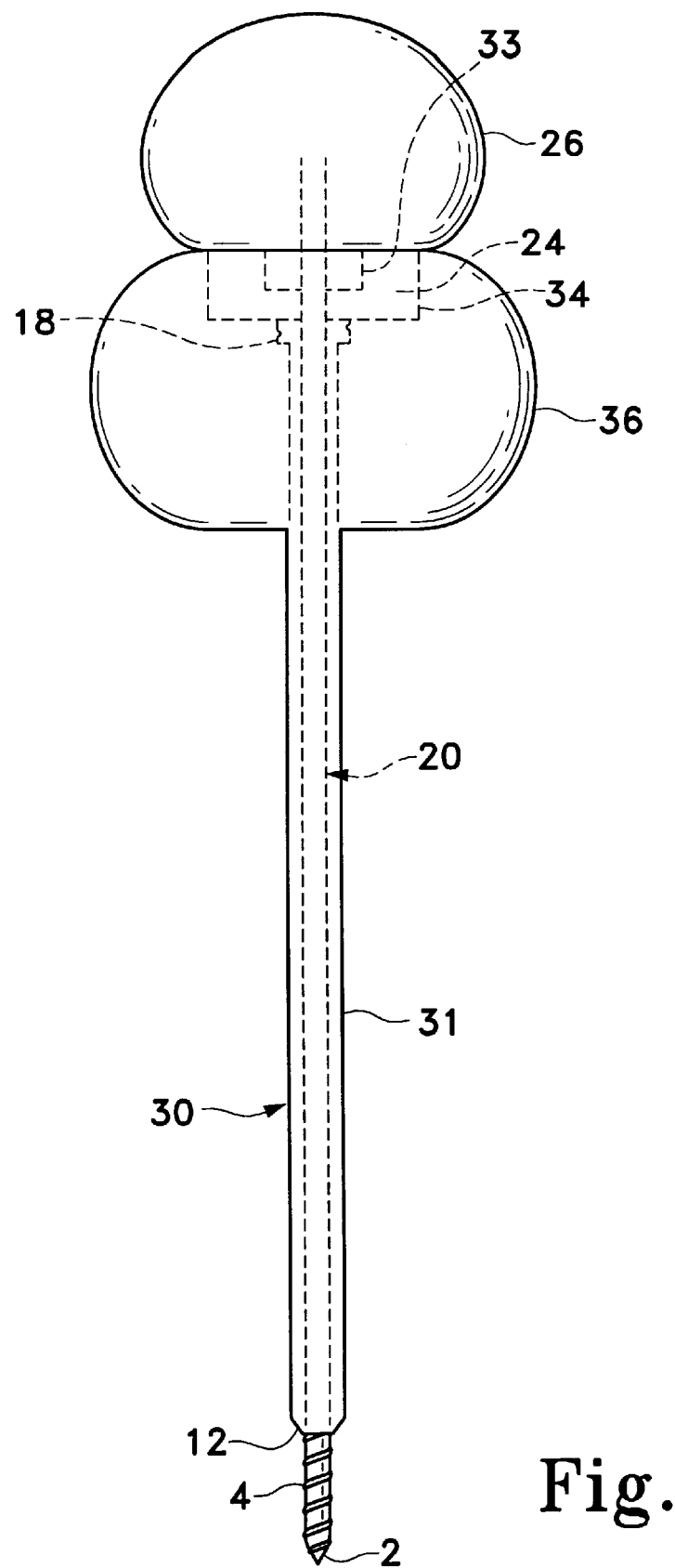
FIG. 2 is a plan view of another embodiment of a depth guided stylet and cannula according to the present invention.

FIG. 2 illustrates an alternative embodiment of a stylet 20 and cannula 30 for similar uses to those described with the embodiment shown in FIG. 1. Stylet 20 includes a tip 2 and self-tapping threads 4, just as in the embodiment of FIG. 1.

The materials employed to make the devices in FIG. 2 are the same as those discussed above with regard to like parts in FIG. 1.

The second or proximal end of the stylet 20 has a handle 26 molded, threaded or otherwise fixed thereto, to enable the operator to torque the stylet about its longitudinal axis with a force applied through a mechanical advantage. Cannula 30 is provided and includes an elongated tubular structure 31 for positioning in the cancellous bone for delivery of PMMA or other bone implant material therein. The tubular structure 31 has an inside diameter which is only slightly larger than the outside diameter of the stylet 20, so that the cannula may effortlessly pass axially over the stylet, while at the same time being supported and guided by the stylet. A first or distal end 12 of the cannula is preferably (but not necessarily) beveled to ease the penetration of the cannula through the cutaneous and soft tissues, and especially through the hard tissues.

A second or proximal end of the cannula preferably has a handle 36 molded, threaded or otherwise fixed thereto, to enable the operator to rotate, torque or push the cannula 30.

Figure 6:
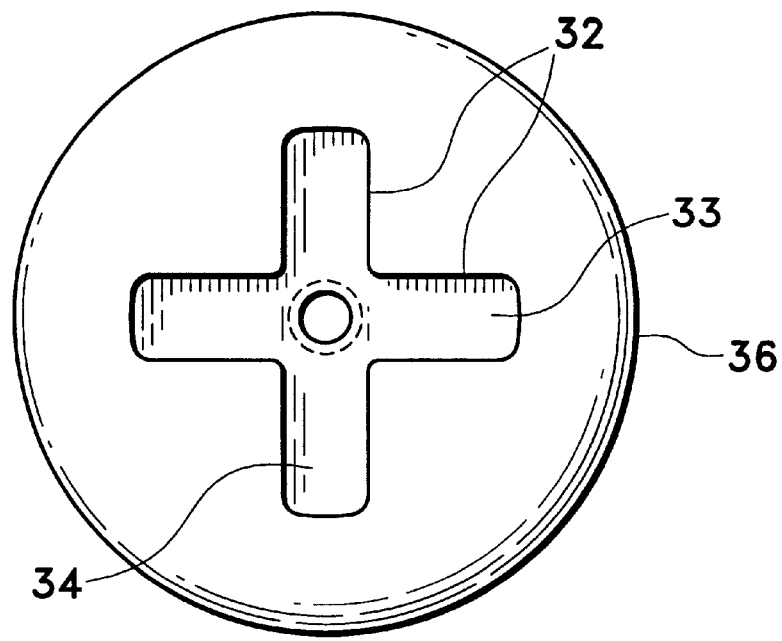
FIG. 6 is a top view of the handle of the cannula shown in FIGS. 2–3.

The inner circumference of the tubular structure of cannula 30 does not have threads for driving the cannula 30 with respect to the stylet 20. Rather, in this embodiment, the cannula is adapted to be slid or pushed along the stylet 20 until it is optimally positioned. Handle 36 is provided with a set of intersecting grooves 32 as shown in the top view in FIG. 6. Preferably, the set of grooves 32 includes a pair of grooves 33,34 intersecting at right angles, for positioning the cannula 30 at two different preset positions along the length of the stylet 20. However, more grooves, or even only one groove may be employed depending upon the number of preset positions that are desired for the cannula 30. Groove 33 is shallower than groove 34 as shown in FIG. 2.

Figure 3:
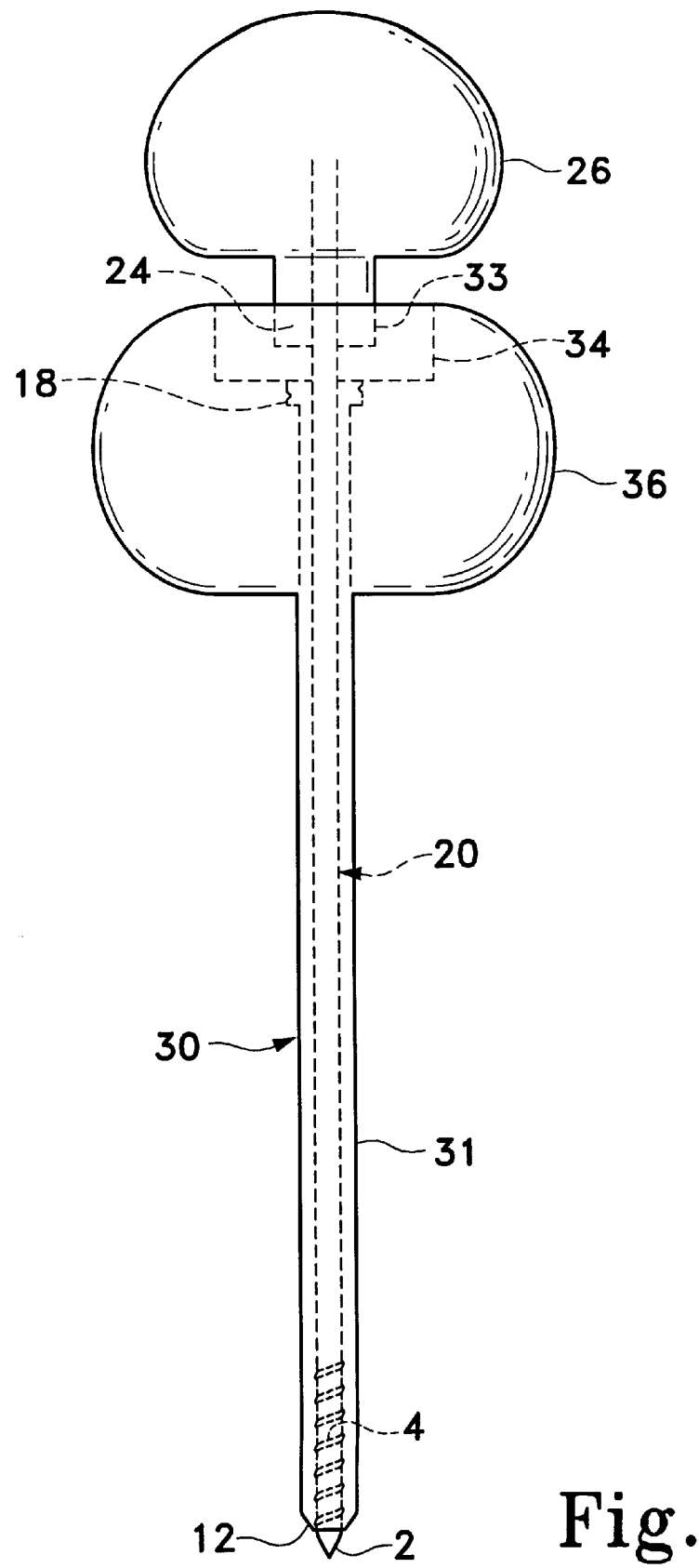
FIG. 3 is an additional view of the invention shown in FIG. 2, with the cannula in a second preset position with respect to the stylet.

Handle 26 includes a protrusion 24 which is sized and dimensioned to fit within each of grooves 33 and 34. In FIG. 2, the cannula 30 is shown in the second preset position, with protrusion 24 fitting within groove 34. FIG. 3 shows the cannula 30 in the first preset position, with protrusion 24 fitting within the shallower groove 33. In this position, the tubular structure 31 substantially covers the distal end of the stylet 20 up to the point 2. Particularly, the self-tapping threads are covered. This position enables the stylet and cannula to be pushed through the soft tissues of the patient with less drag and less damage to the soft tissues of the patient than would result if the self-tapping threads were exposed during this part of the procedure.

Once the stylet tip 2 has penetrated the cortical bone, the operator grasps both handles 26 and 36. Slight retraction of handle 26 away from handle 36 unseats the protrusion 24 from its position in the groove 33, thereby allowing the handles 36 and 26 to be rotated with respect to one another. An approximate ninety degree rotation aligns the protrusion 24 with the groove 34. Handle 36 is then abutted against handle 26, thereby mating protrusion 24 with groove 34. Means are provided for maintaining the protrusion 24 in groove 34 to keep the handles from separating while in the second preset position. For example, the protrusion 24 and groove 34 may be dimensioned so as to provide a friction or snap fit upon mating. Other equivalent means for maintaining the second preset position may be substituted, such as a lip or latching arrangement, not shown. Similar means may be provided to secure the stylet and cannula in the first preset position.

Once in the second preset position, the self-tapping threads 4 become exposed, as shown in FIG. 2. Handle 26 is next torqued in a clockwise direction to engage the self-tapping threads 4 in the cortical bone and begin screwing the stylet 20 through the cortical bone and into the desired position in the cancellous bone. After screwing the stylet 20 into the desired position (e.g., the cancellous tissue of the vertebra) in the hard tissue, as confirmed by viewing the position using an imaging technique referred to above, the operator proceeds to grasp the handle 26 so as to prevent the stylet from rotating further. The cannula is then advanced through the cortical bone and into the desired position within the cancellous bone, by grasping and pushing on the handle 36. Additionally, the handle 36 can be rotated or twisted back and forth to assist in the insertion of the cannula into position.

Although the embodiment shown in FIGS. 2–3 does not provide the same measure of safety and control for advancement of the cannula, it does still afford the safety and control for insertion of the stylet, which is the more likely instrument to be involved in a piercing accident due to the presence of its sharp point 2. As in the previous embodiment, the advancement of the cannula 30, and particularly the beveled end 12 are monitored using an imaging technique to ensure the proper placement of the cannula for injection of the PMMA or other hard tissue implant material. When the beveled end 12 is advanced to a position that is substantially flush with point 2, the operator will cease the advancement of the cannula 30, since it will have reached its optimal position.

The operator next holds the handle 36 in a fixed, non-rotary position, while grasping and pulling the handle 26, so as to retract the stylet 20 from the site, while maintaining the cannula 30 in its position. The operator continues this process until the stylet 20 has been completely removed from within the cannula 30.

An alternative method of inserting the cannula 30 would be to incrementally insert the stylet 20 and the cannula 30. More specifically, the operator could thread the stylet 20 only partially into the cortical bone 103 of the pedicle, and then advance the cannula 30 so as to be substantially flush or close to the tip 2 as described above. Then the operator would again advance the stylet for a small distance through the cortical bone, stop the advancement and follow with advancement of the cannula 30 by the same increment. This type of incremental advancement could be continued until the tip 2 and the beveled end reach the same desired location as described above. Incremental advancement may still further reduce the force that is necessary to be applied to advance the cannula 30 through the cortical bone 103 and thereby increase the safety factor during insertion of the cannula 30. However, the incremental approach is more time consuming, which is a factor that must be considered in deciding whether or not to use the incremental approach.

Surrounding the second end of the tubular structure 31, within the groove 34, is a connector 18 for linking the cannula 30 with a syringe or other tubular supply, for supplying the PMMA or other implantable material that is to be injected via tubular structure 31.

Figure 4:
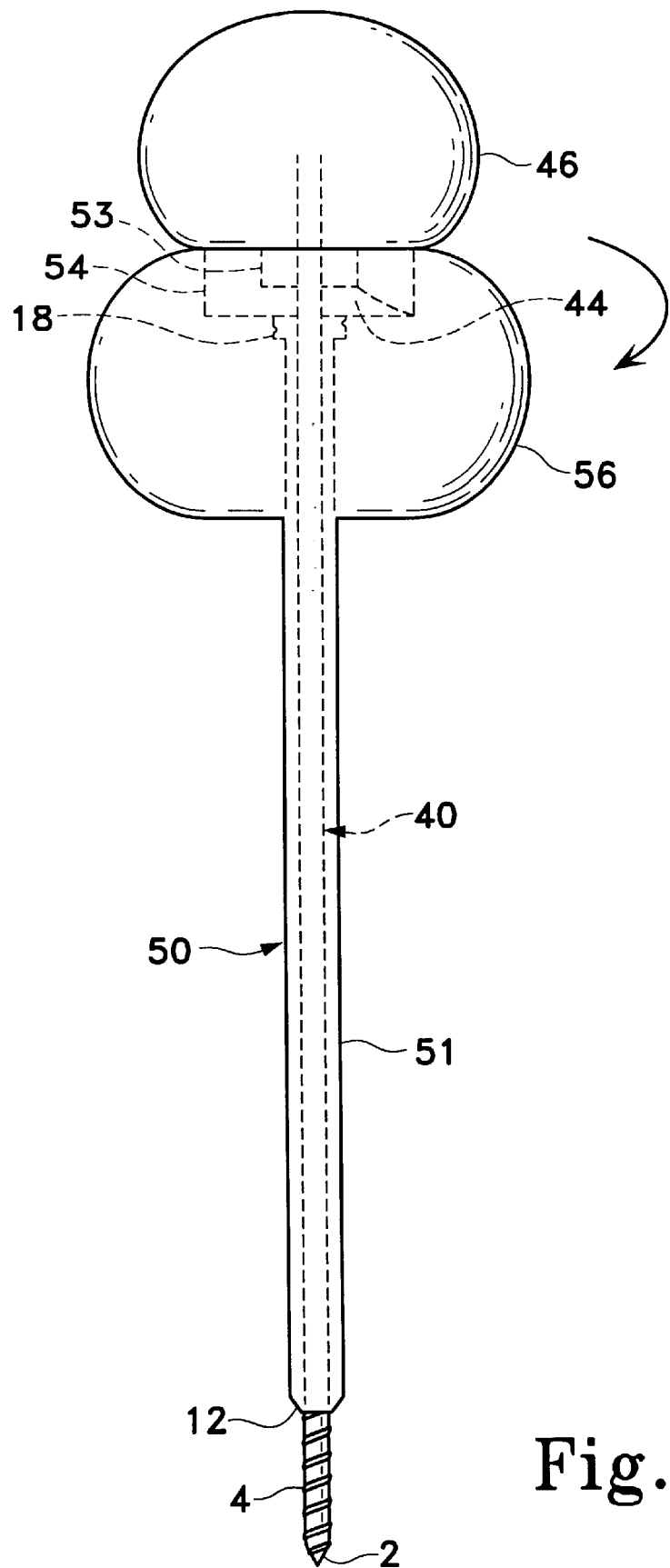
FIG. 4 shows still another embodiment of a depth guided stylet and cannula according to the present invention.

FIG. 4 illustrates another embodiment of a stylet 40 and cannula 50 for similar uses to those described with regard to the previous embodiments. Stylet 40 includes a tip 2 and self-tapping threads 4, just as in the previous embodiments. The materials employed to make the devices in FIG. 4 are the same as those discussed above with regard to like parts in FIGS. 1 and 2.

The second or proximal end of the stylet 40 has a handle 46 molded, threaded or otherwise fixed thereto, to enable the operator to torque the stylet about its longitudinal axis with a force applied through a mechanical advantage. Cannula 50 is provided to include an elongated tubular structure 51 for positioning in the cancellous bone for delivery of PMMA or other bone implant material therein. The tubular structure 51 has an inside diameter which is only slightly larger than the outside diameter of the stylet 40, so that the cannula may effortlessly pass axially over the stylet, while at the same time being supported and guided by the stylet. A first or distal end 12 of the cannula is preferably (but not necessarily) beveled to ease the penetration of the cannula through the cutaneous and soft tissues, and especially through the hard tissues.

Figure 5:
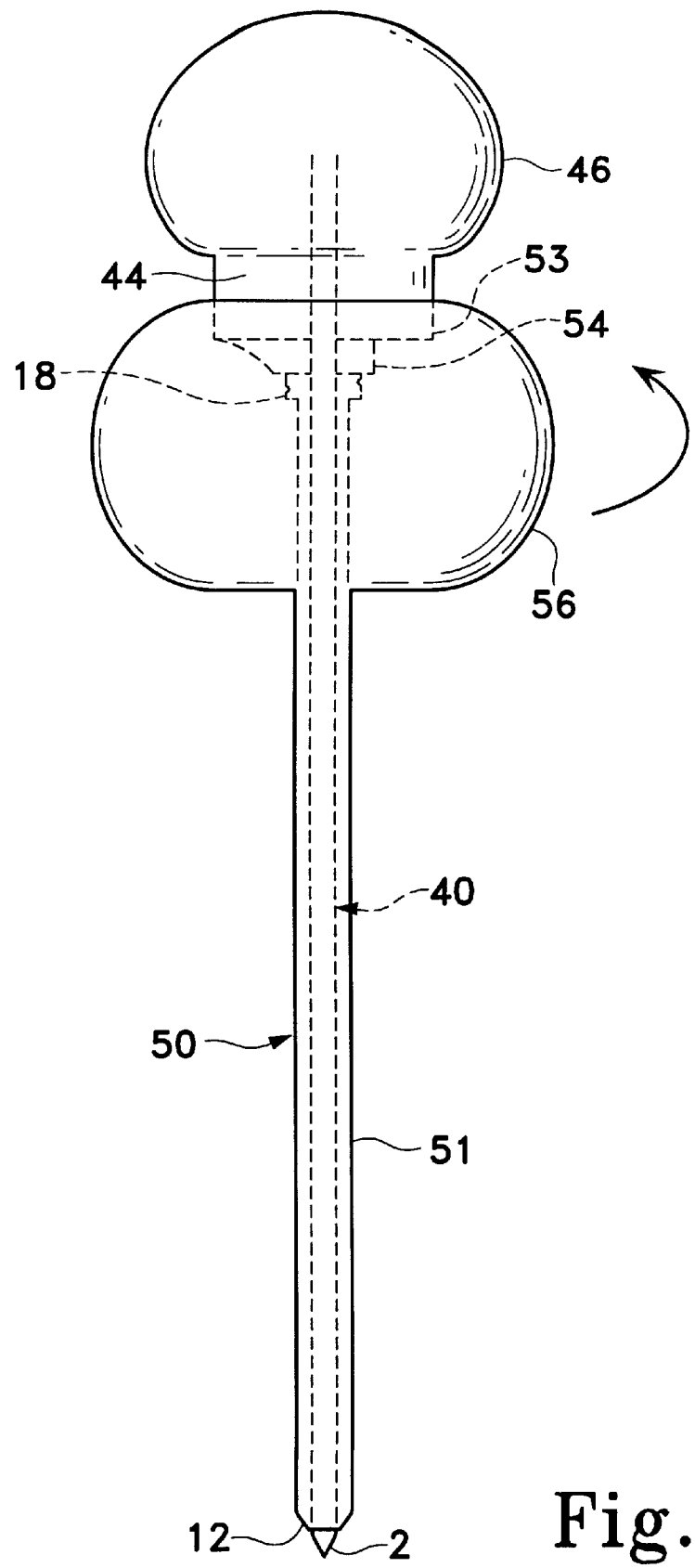
FIG. 5 is an additional view of the invention shown in FIG. 4, with the cannula in a second preset position with respect to the stylet.
Figure 7:
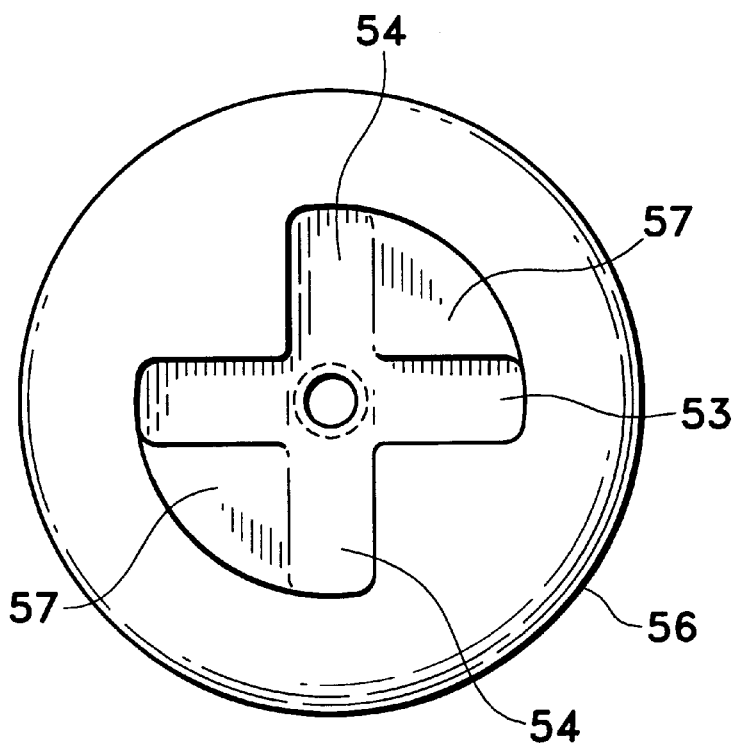
FIG. 7 is a top view of the handle of the cannula shown in FIGS. 4–5.
Figure 8:
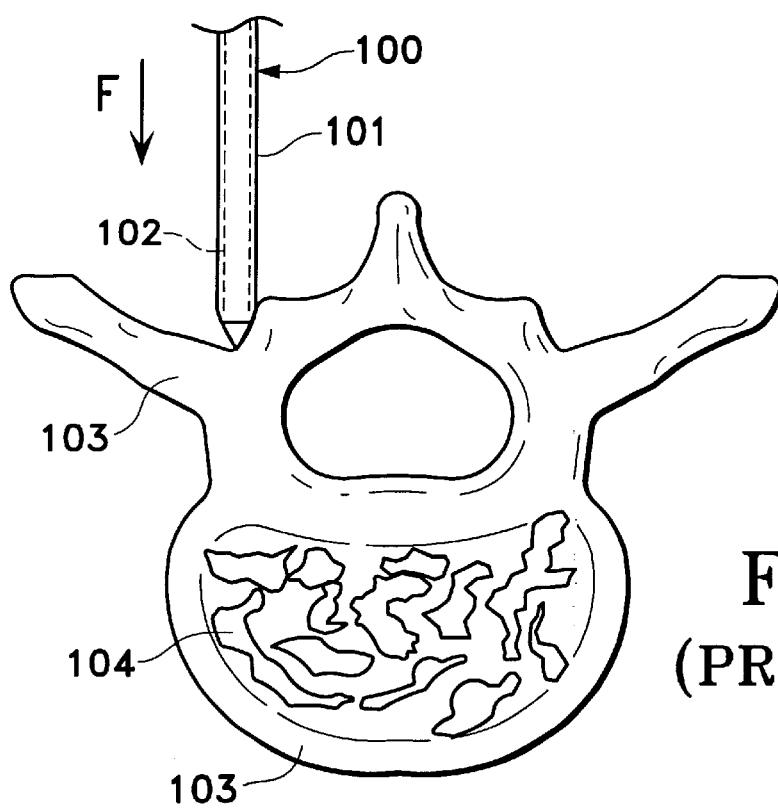
FIGS. 8, 9, 10 and 11 are progressive views illustrating one of the more serious risks involved in a prior art procedure.
Figure 9:
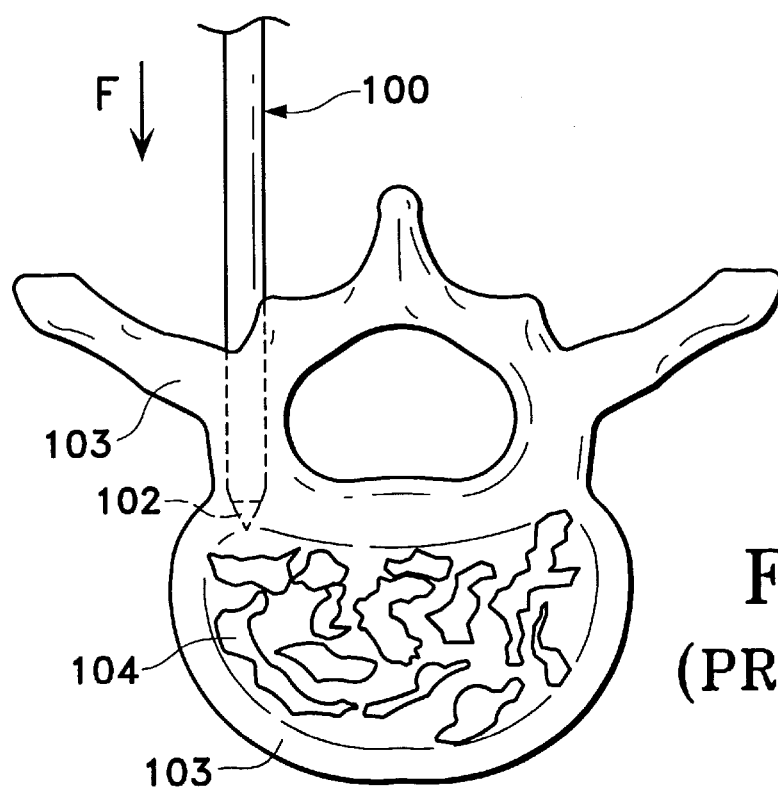
Figure 10:
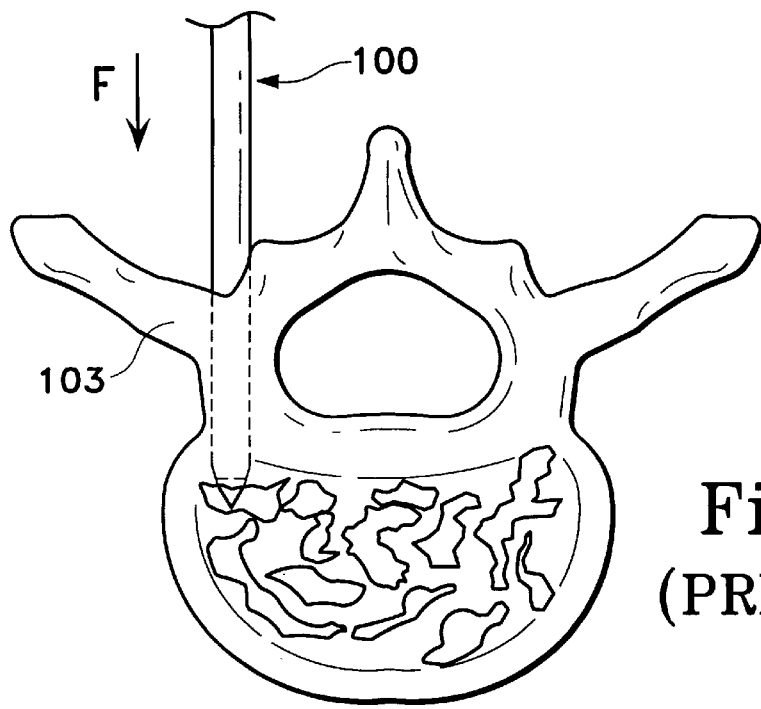
Figure 11:
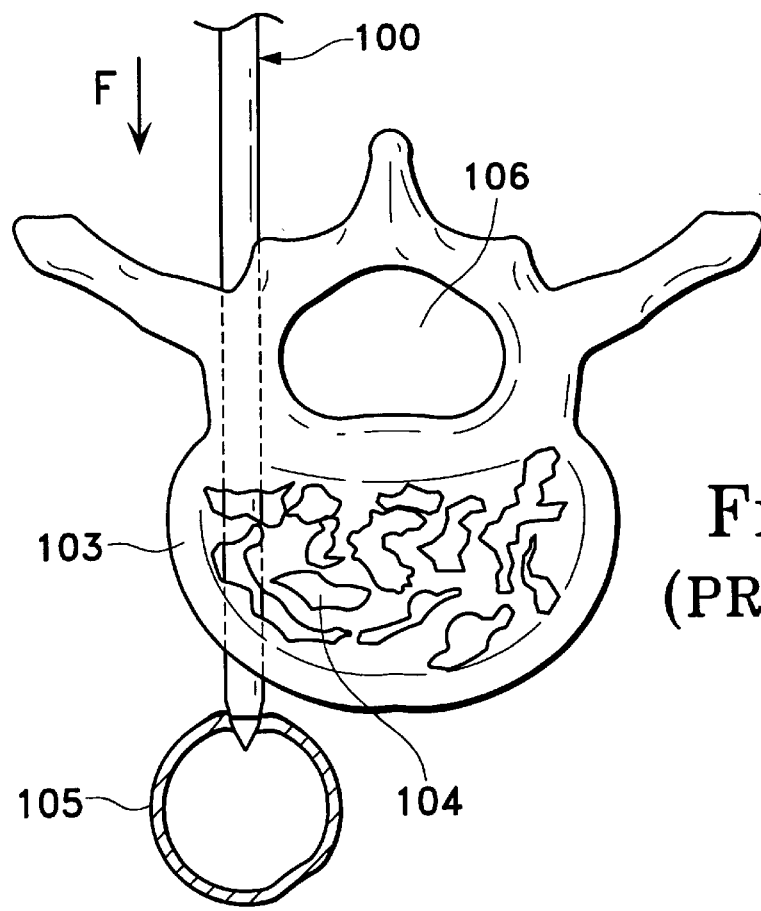

A second or proximal end of the cannula preferably has a handle 56 molded, threaded or otherwise fixed thereto, to enable the operator to rotate, torque or push the cannula 50. Like the embodiment of FIGS. 2–3, the inner circumference of the tubular structure of cannula 50 does not have threads for driving the cannula 50 with respect to the stylet 40. Rather, in this embodiment, the cannula is adapted to be slid or pushed along the stylet 40 until it is optimally positioned. Handle 56 is provided with a set of intersecting grooves 52 as shown in the top view in FIG. 7. Preferably, the set of grooves 52 includes a pair of grooves 53,54 intersecting at right angles, for positioning the cannula 50 at two different preset positions along the length of the stylet 40. However, more grooves, or even only one groove may be employed depending upon the number of preset positions that are desired for the cannula 50. Groove 53 is shallower than groove 54 as shown in FIG. 5.

Handle 46 includes a protrusion 44 which is sized and dimensioned to fit within each of grooves 53 and 54. Between the grooves 53 and 54, the handle 56 is tapered or ramped 57 to allow the protrusion to be moved from groove 53 to groove 54 and vice versa without separating the protrusion 44 from contact with either groove. This is advantageous in that it allows a torquing force to be applied to handle 56 which translates into a driving force to drive the cannula 50 through the cortical bone and into the cancellous bone, as described in further detail below.

In FIG. 4, the cannula 50 is shown in the second preset position, with protrusion 44 fitting within groove 54. FIG. 5 shows the cannula 50 in the first preset position, with protrusion 44 fitting within the shallower groove 53. In this position, the tubular structure 51 substantially covers the distal end of the stylet 40 up to the point 2. Particularly, the self-tapping threads 4 are covered. This position enables the stylet 40 and cannula 50 to be pushed through the soft tissues of the patient with less drag and less damage to the soft tissues of the patient than would result if the self-tapping threads 4 were exposed during this part of the procedure.

Once the stylet tip 2 has penetrated the cortical bone, the operator grasps both handles 46 and 56. By rotating the handle 56 in a clockwise direction while preventing the rotation of the handle 46, the protrusion 44 is repositioned to the deeper groove 54, thereby exposing the self-tapping threads 4, as shown in FIG. 4. Means for securing the protrusion 44 into its respective positions in the grooves 53,54 may be provided to prevent inadvertent displacement of the protrusion 44 and movement of the cannula 50 with respect to the stylet 40. For example, grooves 53 and 54 can be made to be slightly recessed with respect to the ramped surfaces 57.

Handle 46 is next torqued in a clockwise direction to engage the self-tapping threads 4 in the cortical bone and begin screwing the stylet 40 through the cortical bone and into the desired position in the cancellous bone. After screwing the stylet 40 into the desired position (e.g., the cancellous tissue of the vertebra) in the hard tissue, as confirmed by viewing the position using an imaging technique referred to above, the operator proceeds to grasp the handle 46 so as to prevent the stylet from rotating further. The cannula is then advanced through the cortical bone and into the desired position within the cancellous bone, by grasping and rotating the handle 56 in a counterclockwise direction with respect to the handle 46. This causes the protrusion 44 to travel along the ramped surfaces 57 and back into the first preset position shown in FIG. 5. Thus, in this embodiment, rotation of the handle 56 provides a driving force between the protrusion 44 and ramped surfaces 57 that forces the cannula 50 through the cortical bone and into the cancellous bone in the desired location. By predetermining the height differential between the grooves 53 and 54, this embodiment can accurately position the end 12 of the cannula 50 as shown in FIG. 5 to ensure optimum placement of the cannula 50 with respect to the tip 2 that has been optimally placed using imaging feedback. Thus, this embodiment provides a good safety factor both during placement of the stylet 40 as well as the cannula 50.

Surrounding the second end of the tubular structure 51, within the groove 54, is a connector 18 for linking the cannula 50 with a syringe or other tubular supply, for supplying the PMMA or other implantable material that is to be injected via tubular structure 51.

Figure 18:
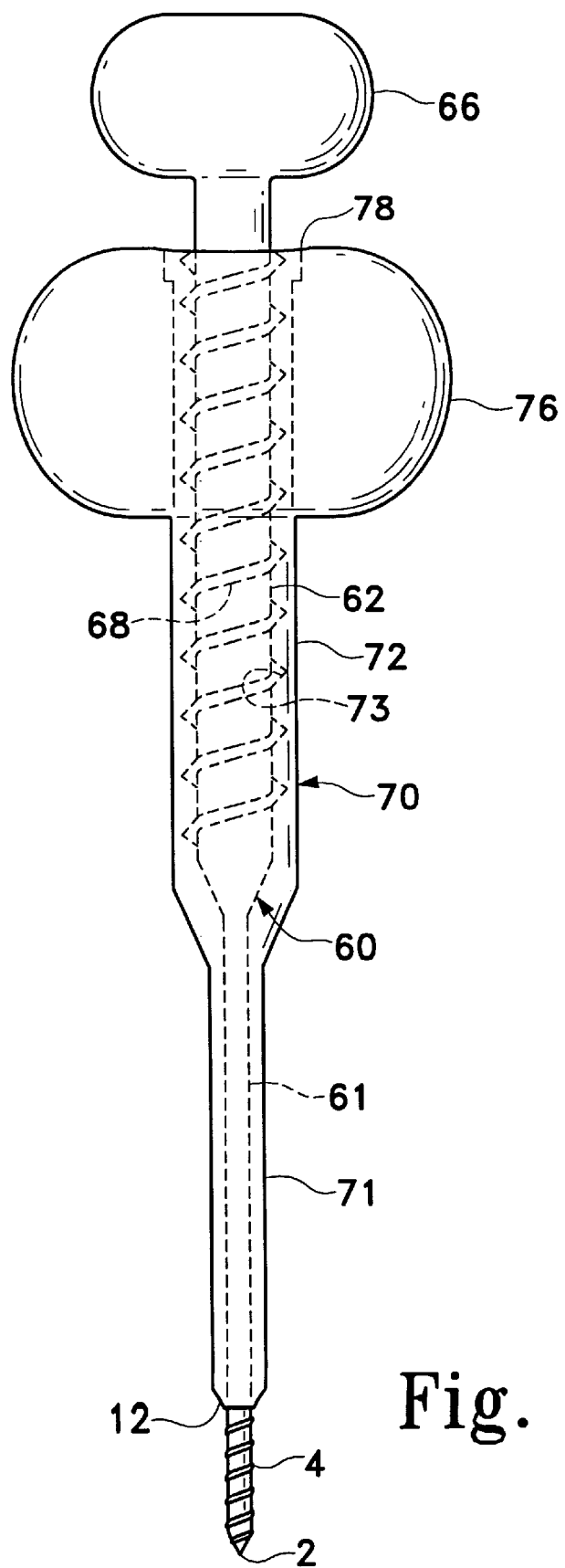
FIG. 18 shows another preferred embodiment according to the present invention.

FIG. 18 shows a variant of the embodiment described with regard to FIG. 1. In order to reduce the substantial amount of pressure that is required to inject PMMA or other bone filler through a standard sized cannula, FIG. 18 shows a modification in which the cannula 70 includes a modified tubular structure design. The first or distal portion 71 of the tubular structure is of the same dimensions as the embodiment of FIGS. 1–2. The second or proximal portion 72 of the cannula 70, however, has a substantially larger diameter than that of the first portion 71. Preferably, the diameter of second portion 72 is about twice the diameter of first portion 71, although any increase in the diameter of second portion 72 over that of the first portion 71 will decrease the pressure requirement for effective delivery of the material to be implanted.

The first and second portions 71,72 have approximately equal lengths, but this is governed by the anatomy of the site to be accessed. In the "average" percutaneous vertebroplasty situation, the first portion 71 is required to be about 1.5" long, as this is the length that is needed for traversing the cortical bone of the pedicle. Thus, the first portion should not be significantly enlarged due to the size constraints of the pedicle, the safety risks to the spinal column and aorta which are increased when the cannula size is increased intravertebrally, and by the desire to remove as little bone as possible when entering with the stylet and cannula, among other factors.

However, the portion of the cannula which will occupy the soft tissues can be significantly expanded without substantially adversely effecting the patient. Given the benefits of reducing the required injection pressure and ensuring a better delivery of the bone implant material, such a modification becomes a viable option.

The devices shown in FIG. 18 operate similarly to that of the embodiment of FIG. 1, i.e., at least a portion of the inner circumference of the second portion 72 is provided with threads 73 which mate with a second set of threads 68 which are provided on the external circumference of a second portion 62 of the stylet 60 distally of threads 4. While the first portion 61 is substantially of the same diameter as the stylet 1 in FIG. 1, the second portion 62 must be substantially larger, preferably twice the diameter of the first portion, to allow threads 68 to mesh with threads 73. The intermeshing of threads 68 and 73 provides a driving and control mechanism for the positioning, advancement and control of the cannula 70 with respect to the stylet 60 and vice versa.

Handle 76 is substantially similar to handle 16 in its design, material, and connection with the tubular structure 71. However, due to the increased diameter of the second portion 72 of the tubular structure 70 and the second portion 62 of the stylet 60, the handle 76 must also have an increased hole through which the second portion 62 of the stylet 60 passes. Handle 66 is substantially similar to handle 6 in its design, material, and connection with the stylet 60.

Surrounding the second end of the tubular structure of the cannula 70 is a connector 78 for linking the cannula 70 with a syringe or other tubular supply, for supplying the PMMA or other implantable material that is to be injected via the cannula 70. Preferably, connector 78 is a Luer-lock type of connector, but other known connecting mechanisms may be successfully interchanged, e.g., a conventional threaded hole, a threads and locking nut arrangement, etc.

Figure 19:
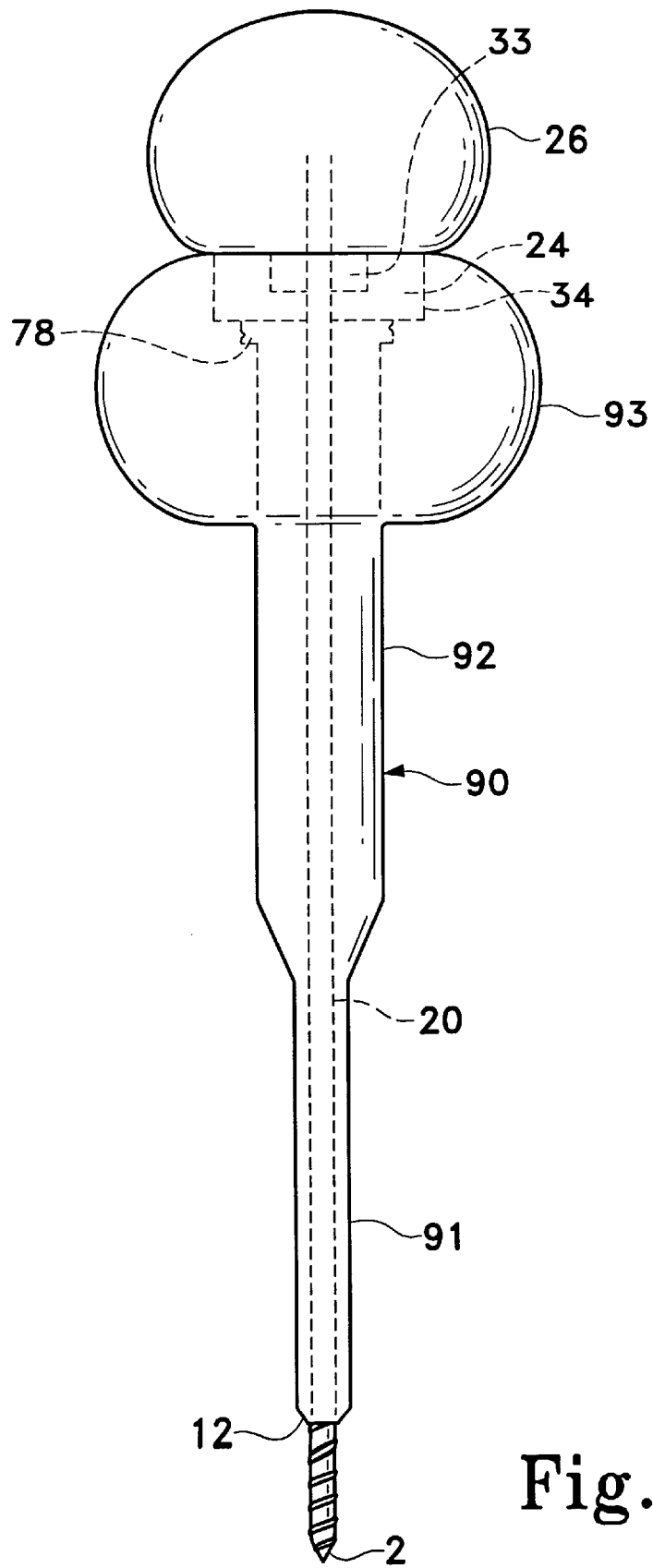
FIG. 19 shows yet another embodiment of the present invention.

The variant shown in FIG. 19 combines the advantages of the embodiment shown in FIGS. 2–3 with the pressure reducing concept described above with respect to FIG. 18. The variant shown in FIG. 19 uses the same stylet 20 but has a cannula 90 which includes a modified tubular structure design. The first or distal portion 91 of the tubular structure is of the same dimensions as the embodiment of FIGS. 1–2. The second or proximal portion 92 of the cannula 90, however, has a substantially larger diameter than that of the first portion 91, similar to the cannula in FIG. 18. Preferably, the diameter of second portion 92 is about twice the diameter of first portion 91, although any increase in the diameter of second portion 92 over that of the first portion 91 will decrease the pressure requirement for effective delivery of the material to be implanted.

The devices shown in FIG. 19 operate similarly to that of the embodiment of FIGS. 1–2 with the added advantage of reduction of the pressure required to deliver the implant material.

Handle 93 is substantially similar to handle 36 in its design, material, and connection with the tubular structure 92. However, due to the increased diameter of the second portion 92 of the tubular structure 90, the handle 93 and grooves 33,34 must also have an increased hole through which the second portion 92 of the cannula 90 passes.

Surrounding the second end of the tubular structure of the cannula 90 is a connector 78 for linking the cannula 90 with a syringe or other tubular supply, for supplying the PMMA or other implantable material that is to be injected via the cannula 90. Preferably, connector 78 is a Luer-lock type of connector, but other known connecting mechanisms may be successfully interchanged, e.g., a conventional threaded hole, a threads and locking nut arrangement, etc.

Figure 20:
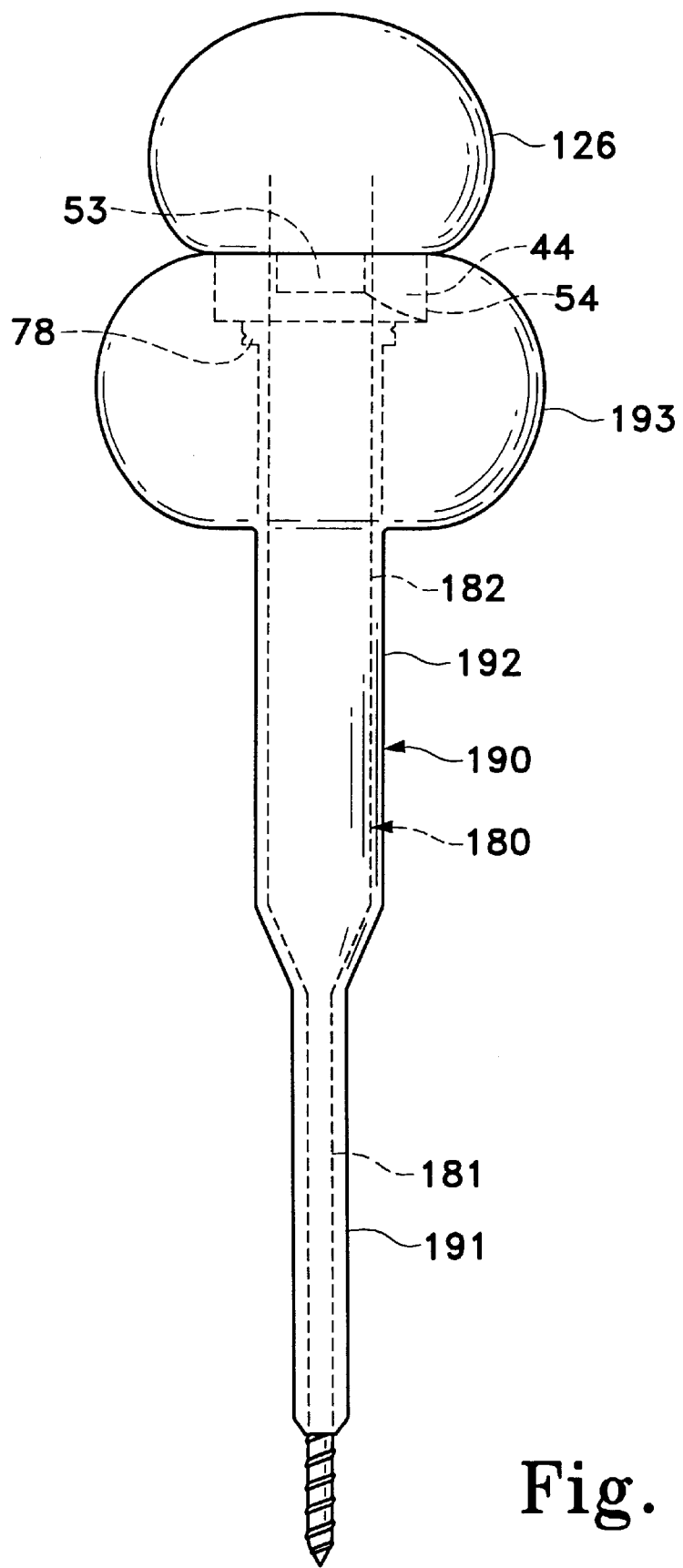
FIG. 20 shows still another embodiment according to the present invention.

The variant shown in FIG. 20 combines the advantages of the embodiment shown in FIGS. 4–5 with the pressure reducing concept described above with respect to FIG. 18. The variant shown in FIG. 20 uses a modified stylet 180 and a cannula 190 which includes a modified tubular structure design. The first or distal portion 191 of the tubular structure is of the same dimensions as the embodiment of FIGS. 1–2. The second or proximal portion 192 of the cannula 190 has a substantially larger diameter than that of the first portion 191, similar to the cannula in FIG. 18. Also similar to the variant of FIG. 18, the second portion 182 of the stylet 180 has a substantially larger diameter than the first portion 181 of the stylet, to substantially conform to the contour of the cannula 190. While the enlarged diameter of the second portion 182 is not necessary for driving the cannula 190, the closer conformance of the components provides a more secure guidance of the cannula 190 along the stylet 180 during driving. It is noted that this type of stylet could also be employed with the variant of FIG. 19 to provide more secure guidance of the cannula 90 during driving. On the other hand, the variant of FIG. 20 could also use a standard stylet like the one shown in FIG. 19 (i.e, without an enlarged diameter second portion) since an enlarged portion is not required for driving in this embodiment.

The devices shown in FIG. 20 operate similarly to that of the embodiment of FIGS. 4–5 with the added advantage of reduction of the pressure required to deliver the implant material.

Handle 193 is substantially similar to handle 56 in its design, material, and connection with the tubular structure 92. However, due to the increased diameter of the second portion 192 of the tubular structure 190 and the second portion 182 of the stylet 180, the handle 193 and grooves 53,54 must also have an increased hole through which the second portion 192 of the cannula 190 passes.

Handle 126 is substantially similar to handle 46 in its design, material, and connection with the stylet portion 182. However, due to the increased diameter of the second portion 182 of the stylet 180, the handle 126 and protrusion 44 must also have an increased hole through which the second portion 182 of the stylet 180 passes.

Surrounding the second end 192 of the tubular structure of the cannula 190 is a connector 78 for linking the cannula 190 with a syringe or other tubular supply, for supplying the PMMA or other implantable material that is to be injected via the cannula 90. Preferably, connector 78 is a Luer-lock type of connector, but other known connecting mechanisms may be successfully interchanged, e.g., a conventional threaded hole, a threads and locking nut arrangement, etc.

Although there have been described above a specific arrangement of devices for percutaneous delivery of a bone implant material, with a limited selected number of alternative embodiments in accordance with the invention for the purpose of illustrating the manner in which the invention may be used to advantage, it will be appreciated that the invention is not limited thereto. Accordingly, any and all modifications, variations or equivalent arrangements which may occur to those skilled in the art should be considered to be within the scope of the invention as set forth in the claims which follow.

What is claimed is:

1. A depth guided stylet comprising:
an elongated rod having first and second ends and a longitudinal axis, said first end terminating in a point adapted for piercing hard tissue;
self-tapping threads extending from said point along said elongated rod for a predetermined distance, said self-tapping threads adapted to self-tap into hard tissue; and
a second set of threads provided on said elongated rod in a location between said self-tapping threads and said handle, wherein said elongated rod comprises a first section having a first diameter, and a second section having a second diameter larger than said first diameter;

wherein said self-tapping threads are provided on said first section, and said second set of threads are provided on said second section; and wherein said second set of threads are adapted to mate with a set of threads within a cannula that fits over said elongated rod.

2. The depth guided stylet of claim 1, further comprising a handle, at least a portion of which radially extends beyond an outer circumference of said elongated rod, provided on said second end for providing a mechanical advantage to a user in rotating said elongated rod about said longitudinal axis.

3. A cannula for use with a depth guided stylet, said cannula comprising:

an elongated tube having first and second ends, said first and second ends being open and adapted for a depth guided stylet to pass therethrough as well as to pass said elongated tube over the depth guided stylet, said first end adapted to closely contour the depth guided stylet to ease penetration of said cannula through tissues as said cannula passes over the depth guided stylet;

a handle attached to said second end of said elongated tube; and a set of intersecting grooves in said handle, said set of intersecting grooves including at least a pair of intersecting grooves having different depths; said grooves adapted to fit over a protrusion on a handle of the depth guided instrument to set the position of said cannula at a predetermined location along the depth guided stylet.

4. The cannula of claim 3, wherein said means for positioning comprise threads along at least a portion of an interior circumference of said elongated tube, said threads adapted to mate with threads on an exterior circumference of the depth guided stylet.

5. The cannula of claim 3, said first end being beveled.

6. A kit adapted to open a pathway into hard tissue, comprising:

a depth guided stylet comprising:
an elongated rod having first and second ends and a longitudinal axis, said first end terminating in a point adapted for piercing hard tissue;
a first positioning element on a predetermimed location of said stylet; and
self-tapping threads extending from said point along said elongated rod for a predetermined distance, said self-tapping threads adapted to self-tap into hard tissue; and a cannula comprising:
an elongated tube having first and second ends, said first and second ends being open and adapted for said depth guided stylet to pass therethrough as well as to allow said elongated tube to pass over said depth guided stylet, said first end having an inside diameter that is only slightly larger than an outer diameter of said elongated rod to ease a penetration of said cannula, through soft tissues and into the hard tissue during movement along said elongated rod toward said first end;
a second positioning element on a predetermined location of said cannula, said second positioning element adapted to interact with said first positioning element to define a position of said cannula with respect to said stylet; and
a handle provided on said second end of said elongated tube,
wherein said first positioning element comprises a protrusion on said handle of said stylet and said second positioning element comprises a set of intersecting grooves in said handle of said cannula, said set of intersecting grooves including at least a pair of intersecting grooves having different depths; said grooves adapted to fit over said protrusion and set the position of said cannula at a predetermined location along said depth guided stylet.

7. The kit of claim 8, further comprising a connector on said handle for connecting said cannula to tubing following removal of said stylet from within said cannula.

8. The kit of claim 7, wherein said connector comprise a Luer lock fitting.

9. The kit of claim 6, wherein said elongated tube comprises a first section having a first diameter, and a second section having a second diameter larger than said first diameter; and wherein said first section is closer than said second section to said first end of said elongated tube.

10. The kit of claim 6, wherein said first end of said elongated tube is beveled to ease the penetration of said cannula through soft and hard tissues.

11. A method of percutaneously implanting a hard tissue implant material comprising:

inserting a stylet having self-tapping treads and cannula percutaneously and through the soft tissues of an organism until abutting hard tissue;

torquing the stylet to engage the self-tapping threads in the hard tissue to draw the stylet through the hard tissue and into a predetermined location within the hard tissue;

advancing the cannula along the stylet to the predetermined position, the cannula having an inside diameter only slightly larger than an outside diameter of the self-tapping threads to ease said advancing the cannula through the hard tissue; and withdrawing the stylet from within the cannula while maintaining the cannula in the predetermined position.

12. The method of claim 11, wherein the cannula has threads along at least a portion thereof and the stylet has a second set of threads that mesh with the threads of the cannula, and said advancing comprises torquing the cannula with respect to the stylet to engage the cannula thread with the second set of threads of the stylet, thereby driving the cannula to the predetermined position.

13. The method of claim 11, wherein the cannula has a beveled end to ease said inserting of the cannula through the soft tissues, as well as to further ease said advancing the cannula through the hard tissue.

14. A kit adapted to open a pathway into hard tissue, comprising:

a depth guided stylet comprising:

an elongated rod having first and second ends and a longitudinal axis, said first end terminating in a point adapted for piercing hard tissue;

a first position element on a predetermined location of said stylet;

self-tapping threads extending from said point along said elongated rod for a predetermined distance, said self-tapping threads adapted to self-tap into hard tissue; and a handle, at least a portion of which radially extends beyond an outer circumference of said elongated rod, thereby providing a mechanical advantage to a user in rotating said elongated rod about said longitudinal axis; and a cannula comprising:
   an elongated tube having first and second ends, said first and second ends being open and adapted for said depth guided stylet to pass therethrough;
   a second positioning element on a predetermined location of said cannula, sad second positioning element adapted to interact with said first positioning element to define a position of said cannula with respect to said stylet; and
   a handle, at least a portion of which radially extends beyond an outer circumference of said elongated tube, thereby providing a mechanical advantage to a user in rotating said elongated tube about a longitudinal axis thereof.

15. A kit adapted to open a pathway into hard tissue, comprising:
   a depth guided stylet comprising:
      an elongated rod having first and second ends and a longitudinal axis, said first end terminating in a point adapted for piercing hard tissue;
      a first positioning element on a predetermined location of said stylet;
      self-tapping threads extending from said point along said elongated rod for a predetermined distance, said self-tapping threads adapted to self-tap into hard tissue; and
      a handle provided on said second end for providing a mechanical advantage to a user in rotating said elongated rod about said longitudinal axis; and
   a cannula comprising:
      an elongated tube having first and second ends, said first and second ends being open and adapted for said depth guided stylet to pass therethrough as well as to allow said elongated tube to pass over said depth guided stylet, said first end having an inside diameter is only slightly larger than an outer diameter of said elongated rod to ease a penetration of said cannula, through soft tissues and into the hard tissue during movement along said elongated rod toward said first end;
      a second positioning element on a predetermined location of said cannula, said second positioning element adapted to interact with said first positioning element to define a position of said cannula with respect to said stylet; and
      a handle provided on said second end of said elongated tube; and
   a connector on said handle of said cannula for connecting said cannula to tubing following removal of said stylet from within said cannula, wherein said connector comprises a Luer lock fitting.

16. A kit adapted to open a pathway into hard tissue, comprising:
   a depth guided stylet comprising:
      an elongated rod having first and second ends and a longitudinal axis, said first end terminating in a point adapted for piercing hard tissue;
      a first positioning element on a predetermined location of said stylet; and
      self-tapping threads extending from said point along said elongated rod for a predetermined distance, said self-tapping threads adapted to self-tap into hard tissue;
      wherein said elongated rod further comprises a first rod section having a first rod diameter, and a second rod section having a second rod diameter larger than said first rod diameter; said self-tapping threads being provided on said first rod section; and
   a cannula comprising:
      an elongated tube having first and second ends, said first and second ends being open and adapted for said depth guided stylet to pass therethrough as well as to allow said elongated tube to pass over said depth guided stylet, said first end having an inside diameter is only slightly larger than an outer diameter of said elongated rod to ease a penetration of said cannula, through soft tissues and into the hard tissue during movement along said elongated rod toward said first end, wherein said elongated tube further comprises a first tube section having a first tube diameter, and a second tube section having a second tube diameter larger than said first tube diameter, said first tube section being closer than said second tube section to said first end of said elongated tube; and
      a second positioning element on a predetermined location of said cannula, said second positioning element adapted to interact with said first positioning element to define a position of said cannula with respect to said stylet;
   wherein said first positioning element comprises a second set of threads provided on said elongated rod in a location between said self-tapping threads and said second end of said elongated rod on said second rod section, and said second positioning element comprises cannula threads along at least a portion of an interior circumference of said elongated tube on said second tube section said cannula threads adapted to mate with said second set of threads.

* * * * *